(12) United States Patent
Eggeling et al.

(10) Patent No.: US 6,177,264 B1
(45) Date of Patent: Jan. 23, 2001

(54) METHOD FOR THE FERMENTATIVE PRODUCTION OF D-PANTOTHENIC ACID USING CORYNEFORM BACTERIA

(75) Inventors: Lothar Eggeling, Jülich; Georg Thierbach, Bielefeld; Hermann Sahm, Jülich, all of (DE)

(73) Assignees: Degussa-Huls Aktiengesellschaft, Marl; Forschunszentrum Julich GmbH, Julich (DE)

( * ) Notice: Under 35 U.S.C. 154(b), the term of this patent shall be extended for 0 days.

(21) Appl. No.: 09/318,794

(22) Filed: May 26, 1999

(30) Foreign Application Priority Data

Dec. 1, 1998 (DE) ................................. 198 55 312

(51) Int. Cl.$^7$ ...................................... C12P 13/00
(52) U.S. Cl. ................ 435/128; 435/252.3; 435/252.32; 435/252.33; 435/419; 435/325; 435/320.1; 435/254.11; 536/23.1; 536/23.2
(58) Field of Search ...................... 536/23.2; 435/320.1, 435/252.3, 254.11, 419, 254.2, 325, 128

(56) References Cited

PUBLICATIONS

Reuter, U. Ber. Forschungszent. Juelich ( Dec. 1998) Juel–3606, pp. 1–115 (Abstract only).*

* cited by examiner

*Primary Examiner*—Ponnathapu Achutamurthy
*Assistant Examiner*—Kathleen Kerr
(74) *Attorney, Agent, or Firm*—Pillsbury Madison & Sutro LLP

(57) ABSTRACT

The invention discloses three polynucleotide sequences for the fermentative production of D-pantothenic acid. These polynucleotide sequences are genes named panB, encoding a ketopantoate hydroxymethyltransferase, panC, encoding pantothenate synthase, and ilvD, encoding dihydroxy-acid dehydratase. The genes panB and panC are found on the same operon, panBC, while the gene ilvD is found in a separate operon. These genes can be used separately or together to enhance the production of D-pantothenic acid in microorganisms, especially in Corynebacterium.

25 Claims, 2 Drawing Sheets

METHOD FOR THE FERMENTATIVE PRODUCTION OF D-PANTOTHENIC ACID USING CORYNEFORM BACTERIA

BACKGROUND OF THE INVENTION

Pantothenic acid is a commercially significant vitamin which is used in cosmetics, medicine, human nourishment and in animal nourishment.

Pantothenic acid can be produced by chemical synthesis or biotechnologically by the fermentation of suitable microorganisms in suitable nutrient solutions. The advantage of the biotechnological production with microorganisms resides in the formation of the desired stereoisomeric D-form of pantothenic acid.

Various types of bacteria such as, for example, *Escherichia coli, Corynebacterium erythrogenes, Brevibacterium ammoniagenes* and also yeasts such as, for example, *Debaromyces castellii* can produce D-pantothenic acid in a nutrient solution containing glucose, DL-pantoic acid and β-alanine, as is shown in EP-A 0,493,060. EP-A 0,493,060 also shows that the formation of D-pantothenic acid is improved in the case of *Escherichia coli* by amplification of pantothenic-acid biosynthetic genes by means of the plasmids pFV3 and pFV5.

EP-A 0,590,857 is relative to strains of *Escherichia coli* which carry resistances against various antimetabolites such as, salicylic acid, α-ketobutyric acid, β-hydroxyaspartic acid, etc. and produce D-pantoic acid and D-pantothenic acid in a nutrient solution containing glucose and β-alanine. EP- 0,590,857 also describes that the production of D-pantoic acid and D-pantothenic acid in *E. coli* can be improved by amplification of pantothenic-acid biosynthetic genes (not defined in detail), from *E. coli* which are contained on the plasmid pFV31.

Moreover, WO 97/10340 shows that the production of pantothenic acid can be further increased in mutants of *Escherichia coli* forming pantothenic acid by elevating the activity of the enzyme acetohydroxy-acid synthesis II, an enzyme of valine biosynthesis.

SUMMARY OF THE INVENTION

The invention addresses the problem of making available novel and improved methods for the fermentative production of D-pantothenic acid with the aid of coryneform bacteria.

The vitamin pantothenic acid is a commercially significant product which is used in cosmetics, medicine, human nourishment and in animal nourishment. There is therefore general interest in making available improved methods of producing pantothenic acid.

When D-pantothenic acid or pantothenic acid or pantothenate are mentioned in the following text not only the free acid but also the salts of D-pantothenic acid such as, for example, the calcium salt, sodium salt, ammonium salt or potassium salt are meant.

Subject matter of the invention includes optionally recombinant DNA from Corynebacterium, which can be replicated in microorganisms of the genus Corynebacterium, containing at least one of the following nucleotide sequences:

a) Encoding the panB gene (ketopantoate hydroxymethyltransferase), in the SEQ ID NO:1, b) Encoding the panC gene (pantothenate synthetase), set forth in SEQ ID NO:1, especially the panBC operon and, if necessary, c) Encoding the ilvD gene (dihydroxy-acid dehydratase), prepared via the SEQ-ID No. 4.

Subject matter of the invention also includes replicative DNA according to cited claim 1 with:

(i) The nucleotide sequences shown in SEQ ID NO:1, SEQ ID NO:4, (ii) Sequences which correspond to variants of the particular sequences (i) within the degeneracy of the nucleic acid code or (iii) Sequences which hybridize with the sequences complementary to particular sequences (i) or (ii), and optionally (iiii) functionally neutral sense mutations in (i).

Coryneform microorganisms, especially of the genus Corynebacterium, transformed by the introduction of one or several replicative DNA pieces are likewise included in the invention.

Subject matter of the invention also includes a method of producing D-pantothenic acid using especially coryneform bacteria which already produce this acid and in which the genes panB and panC are enhanced, in particular by overexpression individually or in combination with one another, optionally combined with a defect mutation in the ilvA gene or with an enhancement of the genes ilvBN, ilvC or ilvD.

The concept "enhancement" describes in this connection the elevation of the intracellular activity of one or several enzymes in a microorganism which are coded by the corresponding DNA in that, for example, the copy number of the gene(s) is increased, a strong promoter is used or a gene is used which codes for a corresponding enzyme with a high activity or optionally a combination of these measures.

The microorganisms constituting the subject matter of the present invention can produce pantothenic acid from glucose, saccharose, lactose, fructose, maltose, molasses, starch, cellulose or from glycerol and ethanol, especially from glucose or saccharose. This involves coryneform bacteria, for example, of the genera Corynebacterium or Arthrobacter. In the genus Corynebacterium the species *Corynebacterium glutamicum* is mentioned in particular, which is known for its ability to form amino acids. This species includes wild-type strains such as, for example, *Corynebacterium glutamicum* ATCC13032, *Brevibacterium flavum* ATCC14067, *Corynebacterium melassecola* ATCC17965 and strains derived from them.

The present inventors discovered that D-pantothenate is produced in an improved manner after enhancement, especially overexpression, of the newly isolated D-pantothenate biosynthetic genes panB and panC individually or in common (panBC operon) from *Corynebacterium glutamicum,* which code for the enzymes ketopantoate hydroxymethyltransferase and pantothenate synthetase.

The inventors further determined that an enhanced expression of the novel valine biosynthetic gene ilvD from *Corynebacterium glutamicum,* which codes for the enzyme dihydroxy-acid dehydratase, contributes to an elevated formation of D-pantothenate. According to the invention, in addition to this gene the enhanced expression of the ilvBN genes, which code for the enzyme acetohydroxy-acid synthase, and of the ilvC gene, which codes for the enzyme isomeroreductase, also brings about an elevated formation of D-pantothenate in *Corynebacterium glutamicum.*

In order to achieve an enhancement (overexpression), for example, the copy number of the corresponding genes is elevated or the promoter and regulation region, which is located upstream from the structural gene, is mutated. Expression cassettes which are inserted upstream from the structural gene operate in the same manner. It is additionally possible to increase the expression in the course of the fermentative formation of D-pantothenate by inducible promoters. The expression is likewise improved by measures for extending the life of m-RNA. Furthermore, the enzymatic activity is likewise enhanced by preventing the degradation of the enzymatic protein. The genes or gene constructs are present thereby either in plasmid vectors with different copy number or are integrated in the chromosome and amplified. Alternatively, an overexpression of the genes concerned can be achieved by altering the composition of the media and conduction of the culture. The expert in the art will find instructions for this in, among others, Martin et al., (Bio/Technology 5, 137–146 (1987)), in Guerrero et al., (Gene 138, 35–41 (1994)), Tsuchiya and Morinaga, (Bio/Technology 6, 428–430 (1988)), in Eikmanns et al., (Gene 102, 93–98 (1991)), in European patent EPS 0,472,869, in U.S. Pat. No. 4,601,898, in Schwarzer and Pühler (Bio/Technology 9, 84–87 (1991)), in Reinscheid et al., (Applied and Environmental Microbiology 60, 126–132 (1994)), in LaBarre et al., (Journal of Bacteriology 175, 1001–1007 (1993)), in the patent application WO 96/15246, in Jensen and Hammer (Biotechnology and Bioengineering 58, 191–195 (1998)) or in the manual "Manual of Methods for General Bacteriology of the American Society for Bacteriology (Washington, D.C., USA, 1981) and in known textbooks of genetics and molecular biology.

In order to isolate the genes panB and panC from *C. glutamicum*, at first a gene bank of this microorganism is established in *E. coli*. The establishment of gene banks is documented in generally known textbooks and manuals. The textbook of Winnacker: German—Genes and Clones, An Introduction to Gene Technology Verlag Chemie, Weinheim, Germany, 1990) or the manual of Sambrook et al.: Molecular Cloning, A Laboratory Manual (Cold Spring Harbor Laboratory Press, 1989) are cited as examples. A known gene bank is that of the *E. coli* K-12 strain W3110 established by Kohara et al. (Cell 50, 495–508 (1987)) in λ vectors. Bathe et al. (Molecular and General Genetics, 252:255–265, 1996) describe a gene bank of *C. glutamicum* ATCC13032 which was established with the aid of the cosmid vector SuperCos I (Wahl et al., 1987, Proceedings of the National Academy of Sciences USA, 84:2160–2164) in the *E. coli* K-12 strain NM554 (Raleigh et al., 1988, Nucleic Acids Research 16:1563–1575). In order to produce a gene bank of *C. glutamicum* in *E. coli*, plasmids such as pBR322 (Bolivar, Life Sciences, 25, 807–818 (1979)) or pUC19 (Norrander et al., 1983, Gene, 26: 101–106) can also be used. Suitable hosts are especially those *E. coli* strains which are restriction-defective and recombination-defective. An example of this is the strain DH5αmcr described by Grant et al., (Proceedings of the National Academy of Sciences USA, 87 (1990) 4645–4649).

The gene bank is subsequently inserted into an indicator strain by transformation (Hanahan, Journal of Molecular Biology 166, 557–580, 1983) or electroporation (Tauch et al., 1994, FEMS Microbiological Letters, 123:343–347). The indicator strain is distinguished in that it comprises a mutation in the gene under consideration which causes a detectable phenotype, for example, an auxotrophy. The indicator strains or mutants are obtainable from published sources or strain collections or are produced themselves, if necessary. In the framework of the present invention the *E. coli* mutant DV39 (Vallari and Rock, Journal of Bacteriology 1985, 164:136–142), which carries a mutation in the panC gene, is especially interesting. Another example of an *E. coli* mutant needing pantothenic acid is the strain SJ2, which carries a mutation in the panB gene and can be ordered from the genetic Stock Center of Yale University (New Haven, Conn., USA). Another example is the *C. glutamicum* mutant R127.7, isolated in the framework of the present invention, which mutant is defective in the ilvD gene coding for dihydroxy-acid dehydratase. After transformation of the indicator strain such as, for example, the panB mutant SJ2 with a recombinant plasmid carrying the gene being considered, such as, for example, the panB gene, and expression of the gene concerned the indicator strain becomes prototrophic relative to the corresponding quality such as, for example, the need for pantothenic acid.

The gene or DNA fragment isolated in this manner can be described and characterized by determination of the sequence as, for example, in Sanger et al., (Proceedings of the National Academy of Sciences of the United States of America USA, 74:5463–5467, 1977).

In this manner the novel DNA sequence of *C. glutamicum* coding for the genes panB and panC was obtained, which is a component of the present invention as SEQ ID NO 1. Furthermore, the amino-acid sequences of the corresponding enzymes were derived from the present DNA sequence with the methods described above. The resulting amino-acid sequence of the panB gene product, namely ketopantoate hydroxymethyltransferase, is shown in SEQ ID NO:2 and in SEQ ID NO:3 the resulting amino-acid sequence of the panC gene product is shown, namely pantothenate synthetase. Furthermore, the novel DNA sequence of *C. glutamicum* coding for the ilvD gene was obtained in this manner, which is a component of the present invention as SEQ ID NO:4. The resulting amino-acid sequence of the ilvD gene product, namely dihydroxy-acid dehydratase, is shown in SEQ ID NO:5.

Coding DNA sequences which are variants of SEQ ID NO:1 and/or SEQ ID NO:4 according to the degeneracy of the genetic code are likewise components of the invention. In the same manner DNA sequences which hybridize with SEQ ID NO:1 and/or SEQ ID NO:4 are components of the invention. Furthermore, in the technical world conservative amino-acid exchanges such as, for example, the exchange of glycine for alanine or of aspartic acid for glutamic acid in proteins are known as sense mutations which do not result in any basic change of the activity of the protein, that is, they are functionally neutral. It is furthermore known that changes on the N- and/or C terminus of a protein do not significantly affect its function in an adverse manner or can even stabilize it. An expert in the art will find information about this in, among other locations, Ben-Bassat et al., (Journal of Bacteriology 169:751–757 (1987)), in O'Regan et al., (Gene 77:237–251 (1989)), in Sahin-Toth et al., (Protein Sciences 3:240–247 (1994)), in Hochuli et al., (Bio/Technology 6:1321–1325 (1988)) and in standard textbooks of genetics and molecular biology. Amino-acid sequences which result in a corresponding manner from SEQ ID NO:2, SEQ ID NO:3 and/or SEQ ID NO:5 are likewise components of the invention.

The gene characterized in this manner can be subsequently brought to expression individually or in combination with others in a suitable microorganism. A known method for expressing or overexpressing genes consists in amplifying them with the aid of plasmid vectors which can be provided in addition with expression signals. Those plasmid vectors which can replicated in the corresponding microorganisms can be considered as plasmid vectors. For *Corynebacterium glutamicum*, for example, the vectors pEKEx1 (Eikmanns et al., Gene 102:93–98 (1991)) or pZ8-1 (European patent 0,375,889) or pEKEx2 (Eikmanns et al., Microbiology 140: 1817–1828 (1994)) or pECM2 (Jäger et al., Journal of Bacteriology 174 (16) : 5462–5465 (1992)) can be considered. Examples of such plasmids are pEKEx2panBC and pECM3ilvBNCD, which are contained in the strains DH5αmcr/pEKEx2panBC and DH5αmcr/pECM3ilvBNCD. Plasmid pEKEx2panBC is an *E. coli/C. glutamicum* shuttle vector which also carries the genes ilvBN and ilvC in addition to the ilvD gene.

The inventors also discovered that the enhancement of the genes panB and panC individually or in combination with the genes ilvBN, ilvC and ilvD has an advantageous effect in those microorganisms which exhibit a reduced synthesis of the amino acids threonine and isoleucine. This reduced synthesis can be achieved by weakening or eliminating the corresponding biosynthesis enzymes and their activities. E.g., the enzymes homoserine dehydrogenase, homoserine kinase, threonine synthase or even threonine dehydratase can be considered for this. A possibility for weakening or eliminating enzymes and their activities are mutagenesis methods.

This includes non-specific methods which make use of chemical reagents such as, for example, N-methyl-N-nitro-N-nitrosoguanidine or UV radiation for the mutagenesis with subsequent searching for the desired microorganisms with a need for L-threonine or L-isoleucine. Methods for mutation initiation and mutant search are generally known and are described, among other places, in Miller (A Short Course in Bacterial Genetics, A Laboratory Manual and Handbook for *Escherichia coli* and Related Bacteria (Cold Spring Harbor Laboratory Press, 1992)) or in the manual "Manual of Methods for General Bacteriology" of the American Society for Bacteriology (Washington, D.C., USA, 1981).

Furthermore, directed recombinant DNA techniques are included. For example, the ilvA gene coding for threonine dehydratase can be deleted in the chromosome with the aid of these methods. Suitable methods for this are described in Schäfer et al., (Gene (1994) 145: 69–73) and Link et al., (Journal of Bacteriology (1998) 179: 6228–6237). In addition, only parts of the gene can be deleted or also mutated fragments of the threonine dehydratase gene can be replaced. A loss or a reduction of the threonine dehydratase activity is achieved in this manner by deletion or replacement (Möckel et al., (1994) Molecular Microbiology 13: 833–842; Morbach et al., (1996) Applied Microbiology and Biotechnology 45: 612–620). An example of such a mutant is the *C. glutamicum* strain ATCC13032ΔilvA, which carries a deletion in the ilvA gene.

The microorganisms produced in accordance with the invention can be cultivated continuously or discontinuously in a batch method (batch cultivation) or in a feed batch method or repeated feed batch method for the purpose of producing pantothenic acid. A summary of known cultivation methods is described in the textbook by Chmiel German—Bioprocessing Technology 1. Introduction to Bioengineering Technology (Gustav Fischer Verlag, Stuttgart, 1991)) or in the textbook of Storhas German—Bioreactors and Peripheral Apparatuses (Vieweg Verlag, Braunschweig/Wiesbaden, 1994)).

The culture medium to be used must satisfy the demands of the particular microorganisms. Descriptions of culture media of various microorganisms are contained in the manual "Manual of Methods for general Bacteriology" of the American Society for Bacteriology (Washington, D.C., USA, 1981). Sugars and carbohydrates such as, for example, glucose, saccharose, lactose, fructose, maltose, molasses, starch and cellulose, oils and fats such as, for example, soy oil, sunflower oil, peanut oil and coconut fat, fatty acids such as, for example, palmitic acid, stearic acid and lineic acid, alcohols such as, for example, glycerol and ethanol and organic acids such as, e.g., acetic acid can be used as carbon source. These substances can be used individually or as a mixture. Organic, nitrogen-containing compounds such as peptones, yeast extract, meat extract, malt extract, corn steep liquor, soybean meal and urea or inorganic compounds such as ammonium sulfate, ammonium chloride, ammonium phosphate, ammonium carbonate and ammonium nitrate can be used as nitrogen source. The nitrogen sources can be used individually or as a mixture. Potassium dihydrogenphosphate or dipotassium hydrogenphosphate or the corresponding sodium-containing salts can be used as phosphorus source. The culture medium must also contain metal salts such as, for example, magnesium sulfate or iron sulfate, which are necessary for growth. Finally, essential growth substances such as amino acids and vitamins can be used in addition to the substances cited above. Moreover, precursors of pantothenic acid such as, for example, aspartate, β-alanine; ketoisovalerate, ketopantoate, pantoate and optionally their salts can be added to the culture medium for an additional increase of the production of pantothenic acid. The cited substances to be used can be added to the culture in the form of a one-time batch or supplied in a suitable manner during the cultivation.

Basic compounds such as sodium hydroxide, potassium hydroxide, ammonia or acidic compounds such as phosphoric acid or sulfuric acid can be added in a suitable manner for controlling the pH of the culture. Anti-foaming agents such as, for example, fatty-acid polyglycolester can be added for controlling the development of foam. In order to maintain the stability of plasmids, suitable, selectively acting substances, for example, antibiotics can be added to the medium. In order to maintain aerobic conditions, oxygen or oxygen-containing gas mixtures such as, for example, air are charged into the culture. The temperature of the culture is normally approximately 20° C. to 50° C. and preferably approximately 25° C. to 45° C. The culture is continued until a maximum of pantothenic acid has formed. This goal is normally achieved within 10 hours to 160 hours.

The concentration of pantothenic acid formed can be determined using known methods (Velisek; Chromatographic Science 60, 515–560 (1992)). Normally, the strain *Lactobacillus plantarum* ATCC8014 is used for the microbiological determination of pantothenic acid (U.S. Pharmacopeia 1980; AOAC International 1980). In addition, even other test organisms such as, for example, Pediococcus acidilactici NCIB6990 are used for the microbiological determination of concentrations of pantothenate (Sollberg and Hegna; Methods in Enzymology 62, 201–204 (1979)).

The following microorganisms were deposited on Oct. 21, 1998 with the German Collection for Microorganisms and Cell Cultures (DSMZ, Mascheroder Weg 1b, D-38124 Braunschweig, Germany) in accordance with the Budapest Convention:

*Escherichia coli* K12 strain DH5αmcr/pEKEx2panBC as DSM12456

*Escherichia coli* K12 strain DH5αmcr/pECM3ilvBNCD as DSM12457

*Corynebacterium glutamicum* ATCC13032ΔilvA as DSM12455

DETAILED DESCRIPTION OF THE INVENTION

The present invention is explained in detail in the following using exemplary embodiments.

EXAMPLE 1

Cloning, sequencing and expression of the genes of pantothenate biosynthesis panB and panC from *C. glutamicum*

1. Cloning of the panB gene and of the panC gene

Chromosomal DNA from *C. glutamicum* ATCC13032 was isolated as described in Schwarzer and Pühler (Bio/Technology 9 (1990) 34–87) and cut with the restriction endonuclease Sau3A. After gel electrophoretic separation DNA fragments were extracted in a size range of 3 to 7 kb and 9 to 20 kb and subsequently ligated into the singular BamHI cleavage site of vector pBR322. The *E. coli* strain DH5αmcr (Grant et al., Proceedings of the National Academy of Sciences of the United States of America USA, 87 (1990) 4645–4649) was transformed with the ligation batches (Hanahan, Journal of Molecular Biology 166 (1983) 557–580). Insert-carrying colonies were identified using their tetracycline sensitivity after being inoculated onto LB agar plates containing 10 μg/ml tetracycline. 8 groups, each of which groups contained 400 plasmids with an insert size of 9 to 20 kb, and 9 groups, each of which contained 500 plasmids with an insert size of 3 to 7 kb, were isolated by plasmid preparations (Sambrook et al, Molecular Cloning. A Laboratory Manual (1989) Cold Spring Harbor Laboratory Press) from combined clones. The *E. coli* panB mutant SJ2 (Cronan et al., 1982, Journal of Bacteriology 149: 916–922) was transformed with this gene bank by means of electroporation (Wehrmann et al., 1994, Microbiology 140: 3349–3356). The transformation batches were plated out directly onto CGXII medium with 15 g/l agar (Keilhauer et al., Journal of Bacteriology (1993) 175: 5595–5603). Plasmid DNA was isolated from clones which were capable of growing without pantothenate supplementation (Sambrook et al., Molecular Cloning. A Laboratory Manual (1989) Cold Spring Harbor Laboratory Press). The ability to complement the panB defect of the *E. coli* mutant SJ2 heterologously was able to be confirmed at 8 plasmids by retransformation.

Figure 1:
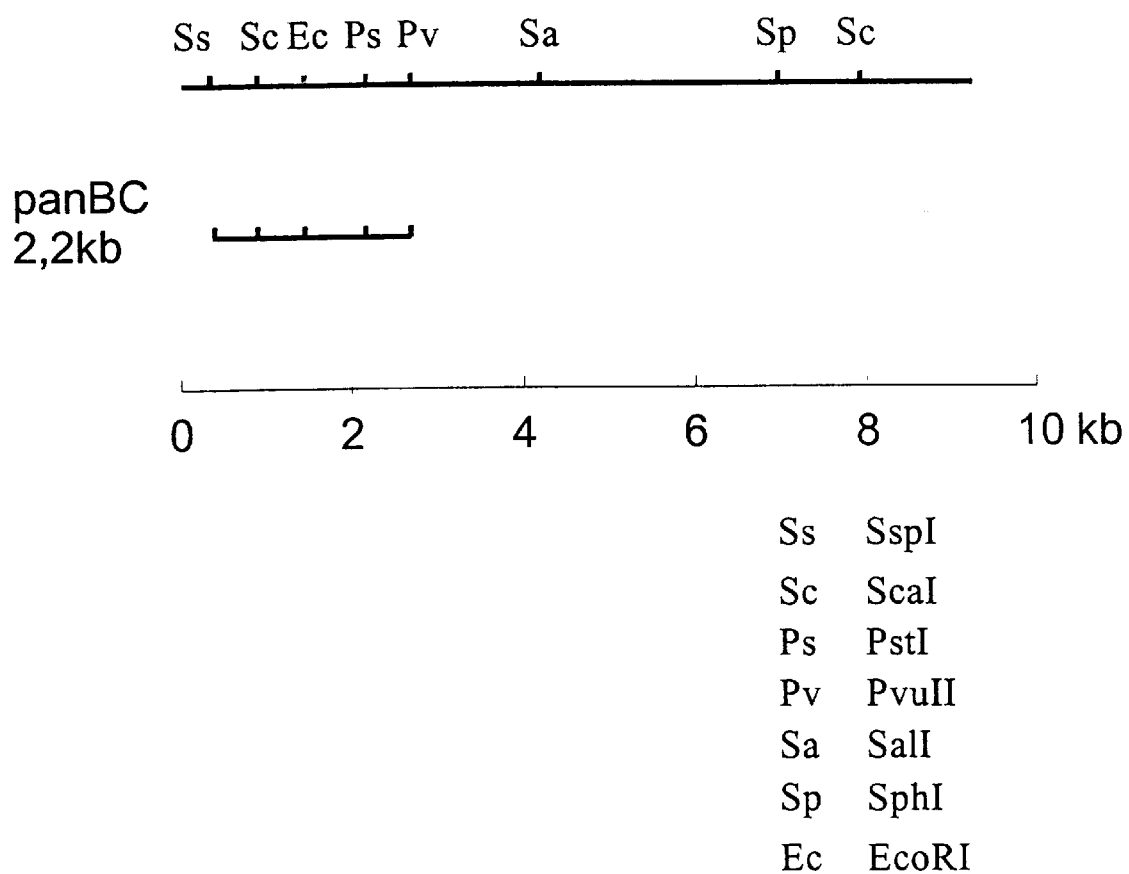
FIG. 1: Restriction map of pURI and position of the sequenced fragment

A restriction mapping was carried out with these 8 plasmids. One of the plasmid vectors investigated, called pUR1 in the following, contained an insert of 9.3 kb in length (FIG. 1). The transformation of the *E. coli* panC mutant DV39 (Vallari and Rock 1985, Journal of Bacteriology 164: 136–142) showed as a result that the vector pUR1 was also capable of complementing the panC defect of this mutant.

2. Sequencing of the panB gene and of the panC gene

A 2.2 kb long fragment of the insert (FIG. 1) of pUR1 was sequenced according to the dideoxy chain-terminating method of Sanger et al. (Proceedings of the National Academy of Sciences of the United States of America USA (1977) 74: 5463–5467). For this, subclones were produced first by means of exonuclease III, which were sequenced with the aid of standard primers (universal and reverse primers of the company Boehringer Mannheim, Germany). The gel electrophoretic analysis of the sequencing batches was carried out with the automatic laser-fluorescence sequencing device (A.L.F.) of Amersham Pharmacia Biotech (Uppsala, Sweden). The nucleotide sequence obtained was analyzed with the program packet HUSAR (release 4.0, EMBL, Cambridge, GB). The nucleotide sequence is set forth in SEQ ID NO:1. The analysis yielded the identification of two open reading frames. An open reading frame 813 bp in length which was identified as panB gene codes for a polypeptide of 271 amino acids and is set forth in SEQ ID NO:2. The second open reading frame, which was identified as panC gene, comprises 837 base pairs. It codes for a polypeptide of 279 amino acids, which is described as SEQ ID NO 3.

3. Expression of the panB gene and of the panC gene

The genes panB and panC were cloned into the *C. glutamicum* expression vector pEKEx2 (Eikmanns et al., 1994, Microbiology 140: 1817–1828 (1994)) in which the two genes are present under the control of the strong tac promoter inducible by IPTG. The cloning was carried out in two steps. At first the start of the panB gene was amplified by PCR. For this, a SalI cleavage site was inserted 19 bp in front of the start codon with the aid of an appropriate primer (primer 1: 5'GATCGTCGACCATCACATCTATACTCAT-GCCC 3' SEQ ID NO:10). The second primer was selected in such a manner that the panB internal EcoRI cleavage site was contained in the amplified fragment (primer 2: 5'ACCCGATGTGGCCGACAACC 3' SEQ ID NO:11). The PCR was carried out with an annealing temperature of 62° C. and the plasmid pUR1 as template according to Sambrook et al., (Molecular Cloning. A Laboratory Manual, Cold Spring Harbor Laboratory Press (1989)). The resulting PCR product 468 bp long was cut with the restriction endonucleases SalI and EcoRI and ligated into the vector pEKEx2 treated in the same manner. The *E. coli* strain DH5αmcr was transformed with the ligation batch. The vector pEKEx2panB' was isolated from a transformant of the type DH5αmcr/pEKEx2panB'.

Figure 2:
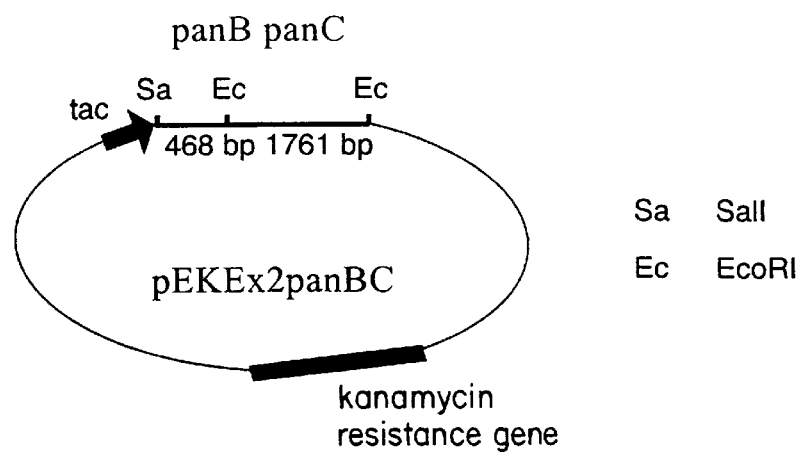
FIG. 2: Restriction map of the plasmid pEKEx2panBC

An EcoRI fragment 1761 bp long and containing the second half of the panBC cluster was now cut out of the plasmid pUR1 by means of restriction digestion. This fragment was cloned into the pEKEx2panB' vector which already contained the panB PCR product and had been linearized previously with EcoRI. The *E. coli* strain DH5αmcr was transformed with the appropriate ligation batch. The vector pEKEx2panBC (FIG. 2) was isolated from a transformant of the type DH5αmcr/pEKEx2panBC in which vector the panBC gene cluster is present under the control of the tac promoter.

EXAMPLE 2

Cloning and sequencing of the ilvD gene from *C. glutamicum* coding for dihydroxy-acid dehydratase

1. Isolation of an ilvD mutant from *C. glutamicum*

The strain *C. glutamicum* R127 (Haynes 1989, FEMS Microbiology Letters 61: 329–334) was mutagenized with N-methyl-N-nitro-N-nitrosoguanidine (Sambrook et al, Molecular Cloning. A Laboratory Manual (1989) Cold Spring Harbor Laboratory Press). For this purpose 5 ml of a *C. glutamicum* culture cultivated overnight were compounded with 250 μl N-methyl-N-nitro-N-nitrosoguanidine (5 mg/ml dimethylformamide) and incubated 30 minutes at 30° C. and 200 rpm (Adelberg 1958, Journal of Bacteriology 76: 326). The cells were subsequently washed twice with sterile NaCl solution (0.9%). Mutants were isolated by replica plating on minimal-medium plates CGXII with 15 g/l agar (Keilhauer et al., Journal of Bacteriology 175: 5595–5603) which mutants only grew when L-valine, L-isoleucine and L-leucine were added (0.1 g/l each).

The enzymatic activity of the dihydroxy-acid dehydratase was determined in the raw extract of these mutants. For this, the clone was cultivated in 60 ml LB medium and centrifuged off in the exponential growth phase. The cell pellet was washed once with 0.05 M potassium phosphate buffer and resuspended in the same buffer. The cellular maceration took place by means of a 10-minute treatment with ultrasound (Branson-Sonifier W-250, Branson Sonic Power Co., Danbury, USA). The cell fragments were subsequently separated by a 30-minute centrifugation at 13000 rpm and 4° C. and the supernatant used as raw extract in the enzyme test. The reaction batch of the enzyme test contained 0.2 ml 0.25

M TRIS/HCl, pH 8, 0.05 ml raw extract and 0.15 ml 65 mM alpha,β-dihydroxy-β-methylvalerate. The test batches were incubated at 30° C., 200 µl specimens taken after 10, 20 and 30 minutes and their concentration of ketomethylvalerate determined with HPLC analytic chemistry (Hara et al., 1985, Analytica Chimica Acta 172: 167–173). As Table 1 shows, strain R127/7 exhibits no dihydroxy-acid dehydratase activity, in contrast to which isomeroreductase and acetohydroxy-acid synthase activities are still present as further enzymes of the synthesis of the branched-chain amino acids.

TABLE 1

Specific activities (µmol/min and mg protein) of different enzymes in C. glutamicum strains

| Strain | Dihydroxy-acid dehydratase | Isomero reductase | Acetohydroxy-acid synthase |
|---|---|---|---|
| R127 | 0.003 | 0.05 | 0.07 |
| R127/7 | 0.000 | 0.06 | 0.09 |

2. Cloning of the ilvD gene from C. glutamicum

Chromosomal DNA from C. glutamicum R127 was isolated as described in Schwarzer and Pühler (Bio/Technology 9 (1990) 84–87). It was cleaved with the restriction enzyme Sau3A (Boehringer Mannheim) and separated by saccharose density gradient centrifugation (Sambrook et al., Molecular Cloning. A Laboratory Manual (1989) Cold Spring Harbor Laboratory Press). The fraction with the fragment-size range of approximately 6–10 kb was used for ligation with the vector pJC1 (Cremer et al., Molecular and General Genetics 220 (1990) 478–480). The vector pJC1 was linearized for this with BamHI and dephosphorylized. Five ng thereof were ligated with 20 ng of the cited fraction of chromosomal DNA and the mutant R127/7 transformed therewith by electroporation (Haynes and Britz, FEMS Microbiology Letters 61 (1989) 329–334). The transformants were tested for the ability to grow on CGXII agar plates without the addition of the branched-chain amino acids. Of over 5000 transformants tested, 8 clones grew after replica plating and a two-day incubation at 30° C. on minimal-medium plates. Plasmid preparations from these clones were carried out as described in Schwarzer et al., (Bio/Technology (1990) 9: 84–87). Restriction analyses of the plasmid DNA showed that the same plasmid, called pRV in the following, was contained in all 8 clones. The plasmid carries an insert of 4.3 kb and was tested by retransformation for its capacity to complement the ilvD mutant R127/7. The range responsible for the complementation of mutant R127/7 was limited to a 2.9 kb ScaI/XhoI fragment by subcloning.

3. Sequencing of the ilvD gene

The nucleic-acid sequence of the 2.9 kb ScaI/XhoI fragment was carried out according to the dideoxy chain-terminating method of Sanger et al. (Proceedings of the National Academy of Sciences of the United States of America USA (1977) 74: 5463–5467). The auto-read sequencing kit was used (Amersham Pharmacia Biotech, Uppsala, Sweden). The gel electrophoretic analysis took place with the automatic laser fluorescence sequencing device (A.L.F.) of Amersham Pharmacia Biotech (Uppsala, Sweden). The nucleotide sequence obtained was analyzed with the program packet HUSAR (release 4.0, EMBL, Cambridge, GB). The nucleotide sequence is set forth in ID SEQ NO:4. The analysis yielded an open reading frame of 1836 base pairs which was identified as ilvD gene and codes for a polypeptide of 612 amino acids which is described as SEQ ID NO:5.

EXAMPLE 3

Construction of an ilvA deletion mutant from C. glutamicum

The insertion of a deletion into the ilvA gene from Corynebacterium glutamicum ATCC13032 was carried out with the system for gene exchange described in Schäfer et al. (Gene 145: 69–73 (1994)). For the construction of the inactivation vector pK19mobsacBΔilvA, an internal 241 bp BglII fragment was first removed from the ilvA gene present on an EcoRI fragment in vector pBM21 (Möckel et al., 1994, Molecular Microbiology 13: 833–842). For this, the vector was cleaved with BglII and religated after separation of the ilvA internal BglII fragment by means of agarose gel electrophoresis. The incomplete gene was subsequently isolated from the vector as EcoRI fragment and ligated into the vector pK19mobsacB linearized with EcoRI (Schäfer 1994, Gene 145: 69–73). The inactivation vector pK19mobsacBΔilvA obtained was introduced by transformation into the E. coli strain S 17-1 (Hanahan 1983, Journal of Molecular Biology 166: 557–580) and transferred per conjugation to C. glutamicum ATCC13032 (Schafer et al. 1990, Journal of Bacteriology 172: 1663–1666). Kanamycin-resistant clones of C. glutamicum were obtained in which the inactivation vector was present integrated in the genome. In order to select for the excision of the vector, kanamycin-resistant clones were plated out onto saccharose-containing LB medium (Sambrook et al.: Molecular Cloning, A Laboratory Manual (1989) Cold Spring Harbor Laboratory Press) with 15 g/l agar, 2 % glucose/10 % saccharose) and colonies were obtained which lost the vector again by a second recombination event (Jäger et al. 1992, Journal of Bacteriology 174: 5462–5465). 36 clones were isolated by being inoculated onto minimal medium plates (medium CGXII with 15 g/l agar (Keilhauer et al., Journal of Bacteriology 175 (1993) 5595–5603) with and without 2 mM L-isoleucine and with and without 50 µg/ml kanamycin which clones were kanamycin-sensitive and isoleucine-auxotrophic by virtue of the excision of the vector and in which the incomplete ilvA gene (ΔilvA-allele) was now present in the genome. One of these clones was designated as strain ATCC13032ΔilvA and used further.

EXAMPLE 4

Expression of the genes ilvBN, ilvC and ilvD in C. glutamicum

The genes of acetohydroxy-acid synthase (ilvBN) and of isomeroreductase (ilvC) (Cordes et al 1992, Gene 112: 113–116 and Keilhauer et al. 1993, Journal of Bacteriology 175: 5595–5603) and of dihydroxy-acid dehydratase (ilvD) (example 2) were cloned for expression into vector pECM3. Vector pECM3 is a derivative of pECM2 (Jäger et al. 1992, Journal of Bacteriology 174: 5462–5465), which arose by deletion of the BamHI/BglII DNA fragment approximately 1 kbp long carrying the kanamycin-resistance gene.

Figure 3:
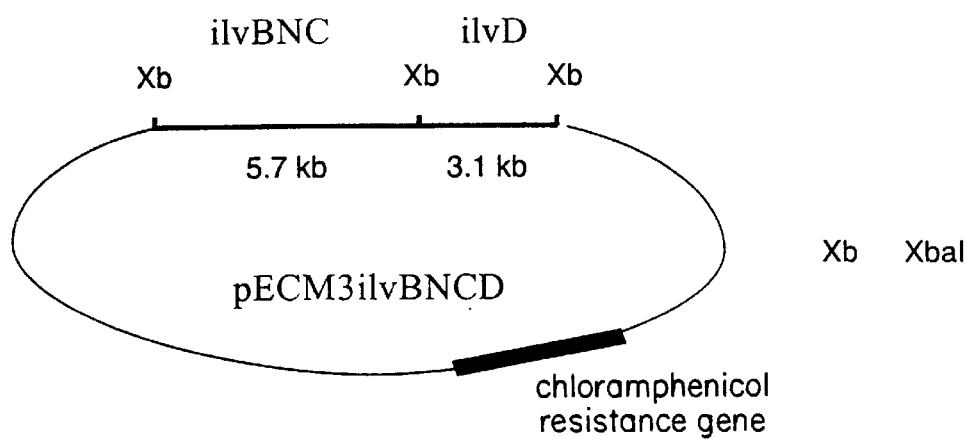
FIG. 3: Restriction map of the plasmid pECM3ilvBNCD

In vector pKK5 (Cordes et al. 1992, Gene 112: 113–116) the genes ilvBNC were already present in cloned form in vector pJC1 (Cremer et al. 1990 Molecular and General Genetics 220: 478–480). A 5.7 kb XbaI-ilvBNC fragment was isolated from the latter and introduced together with a 3.1 kb-XbaI fragment of vector pRV, which fragment contained the ilvD gene, into the vector pECM3 linearized with XbaI. The ligation batch was transformed thereby into the E. coli strain DH5αmcr. The plasmid pECM3ilvBNCD was obtained from a transformant of the type DH5αmcr/pECM3ilvBNCD (FIG. 3).

The plasmid pEMC3ilvBNCD was introduced into the strain ATCC13032ΔilvA by electroporation (Haynes 1989, FEMS Microbiology Letters 61: 329–334) and selection made for chloramphenicol resistance and the strain ATCC13032ΔilvA/pECM3ilvBNCD obtained. Furthermore, the plasmid pEKEx2panBC was introduced into the strain ATCC13032 and into the strain ATCC13032ΔilvA by means of electroporation (Haynes 1989, FEMS Microbiology Letters 61: 329–334) and selection made for kanamycin resistance and the strains ATCC13032/pEKEx2panBC and ATCC 13032ΔilvA/pEKEx2panBC obtained. The plasmids pEKEx2panBC and pEKEX2 were introduced into the strain ATCC13032ΔilvA/pECM3ilvBNCD by electroporation (Haynes 1989, FEMS Microbiology Letters 61: 329–334) and selection for kanamycin and chloramphenicol. The strains ATCC13032ΔilvA/pECM3ilvBNCD pEKEX2 and ATCC13032ΔilvA/pECM3ilvBNCD pEKEx2panBC were produced in this manner.

EXAMPLE 5

Construction of a panC mutant of *C. glutamicum* requiring pantothenic acid

A *C. glutamicum* R127 panC mutant was produced with the aid of the inactivation vector pK18mob (Schäfer et al. 1994, Gene 145: 69–73).

For the construction of the panC inactivation vector a central fragment, 168 bp in size, of the panC gene (nucleotide 265–432 of the gene comprising 837 bp) of *C. glutamicum* was first amplified by polymerase chain reaction (PCR). The vector pUR1 functioned here as template (see example 6); two 20mers, primer 1 and primer 2 were used as primers: Primer 1 5'GTTCGCACCCGATGTGGAGG 3' (SEQ ID NO: 12), primer 2 5'ATGCACGATCAGGGCG-CACC 3' (SEQ ID NO:13). The PCR was carried out according to Sambrook et al.: (Molecular Cloning, A Laboratory Manual (1989) Cold Spring Harbor Laboratory Press) with an annealing temperature of 55° C. The fragment obtained was ligated after intermediate cloning into the SmaI cleavage site of the vector pUC18, directed as EcoRI/SalI fragment into the inactivation vector pK18mob (Schäfer et al. 1994, Gene 145:69–73). Vector pK18mob'panC' obtained in this manner was used for the transformation of the *E. coli* strain S 17-1 and subsequently introduced per conjugation into *C. glutamicum* R127. In this manner clones from *C. glutamicum* R127 were obtained by selection for kanamycin resistance in which clones the integration vector is integrated into the panC gene by a homologous recombination event. Strain R127panC::pK18mob'panC', obtained in this manner, is suitable for determining D-pantothenate.

EXAMPLE 6

Quantitative determination of D-pantothenate

The *C. glutamicum* panC mutant R127panC::pK18mob'panC' was constructed for the quantitative determination of D-pantothenate (see example 5), the growth of which [mutant] is a direct function of the concentration of D-pantothenate of the medium. This strain is pantothenic-acid-auxotrophic and exhibits no growth upon supplementation with β-alanine and D-pantoate.

In order to determine pantothenate with this indicator, strain CGXII medium (Keilhauer et al., Journal of Bacteriology (1993) 175: 5595–5603) was used as test medium. For this, each 3 ml CGXII medium concentrated 4/3 times was compounded in an incubation tube (Falcon 2057, Becton and Dickinson, N.J., USA) with 1 ml sterile calibrating solution or solution to be tested containing pantothenic acid and inoculated with the indicator strain. 60 μl of a glycerol culture of the indicator strain were used as inoculum in each instance. After a 40-hour incubation at 30° C. the cell density ($OD_{600}$) (Novaspec 4049 spectrophotometer, LKB Biochrom, Cambridge, GB) of the test batches was determined and the concentration of pantothenic acid established by means of a calibrating curve. The strain exhibits up to a concentration of 25 μg/l, a linear dependency of the growth on the concentration of pantothenic acid at an optical density of 0.5 to 10. In order to produce the glycerol culture of the indicator strain this strain was incubated on unsupplemented CGXII medium for 24 hours (starvation of D-panthothenate). 1050 μl of the culture were subsequently compounded with 700 μl glycerol. 60 μl of this glycerol culture frozen intermediately at –70° C. were used to determine D-pantothenate, as described before. Na panthothenate was used as reference, which was obtained from the Sigma company (Deisenhofen, Germany).

EXAMPLE 7

Production of D-pantothenate with various *C. glutamicum* strains

In order to investigate their formation of panthothenate the strains ATCC13032, ATCC13032/pEKEx2panBC, ATCC13032ΔilvA and ATCC13032ΔilvA/pEKEx2panBC were precultivated in 60 ml brain heart infusion medium (Difco Laboratories, Detroit, USA) for 14 hours at 30° C. The cells were subsequently washed twice with 0.9 % NaCl solution (w/v) and each 60 ml CGXII medium inoculated with this suspension in such a manner that the $OD_{600}$ was 0.5. The medium was identical with the medium described in Keilhauer et al., (Journal of Bacteriology (1993) 175: 5595–5603) but contained 2 mM L-isoleucine in addition. The medium CGXII described by Keilhauer et al. Is shown in Table 2.

TABLE 2

| Composition of the medium CGXII | |
|---|---|
| Component | Concentration |
| $(NH_4)_2SO_4$ | 20 g/l |
| urea | 5 g/l |
| $KH_2PO_4$ | 1 g/l |
| $K_2HPO_4$ | 1 g/l |
| $Mg_2O_4*7\ H_2O$ | 0.25 g/l |
| 3-morpholinopropane sulfonic acid | 42 g/l |
| $CaCl_2$ | 10 mg/l |
| $FeSO_4*7\ H_2O$ | 10 mg/l |
| $MnSO_4*\ H_2O$ | 10 mg/l |
| $ZnSO_4*7\ H_2O$ | 1 mg/l |
| $CuSO_4$ | 0.2 mg/l |
| $NiCl_2*6\ H_2O$ | 0.02 mg/l |
| biotin (pH 7) | 0.2 mg/l |
| glucose | 40 g/l |
| protocatechinic acid | 0.03 mg/l |

During the cultivation of the strains ATCC13032/pEKEx2panBC and strain ATCC13032ΔilvA/pEKEx2panBC, the medium was additionally compounded after 5 hours with 1 mM isopropylthio-β-D-galactoside. After 24 hours of cultivation specimens were taken, the cells centrifuged off and the supernatant sterilized by filtration. The concentration of pantothenate of the supernatant was determined with the aid of the pantothenate test described in example 6. The results are shown in Table 3.

TABLE 3

Formation of D-pantothenate in various C. glutamicum strains

| Strain | D-pantothenate (mg/l) |
|---|---|
| ATCC13032 | 0.01 |
| ATCC13032/pEKEx2panBC | 0.03 |
| ATCC13032ΔilvA | 0.06 |
| ATCC13032Δi1vA/pEKEx2panBC | 0.3 |

EXAMPLE 8

Production of D-pantothenate with various *C. glutamicum* strains with the addition of β-alanine In order to quantify the formation of pantothenate the strains ATCC13032ΔilvA/pECM3ilvBNCD pEKEx2 and ATCC13032ΔilvA/pECM3ilvBNCD pEKEx2panBC were precultivated in 60 ml brain heart infusion medium (Difco Laboratories, Detroit, USA) with 25 mg/l kanamycin and 3 mg/l chloramphenicol for 14 hours at 30° C., washed twice with 0.9 % NaCl solution (w/v) and each 60 ml CGXII medium inoculated with this suspension in such a manner that the $OD_{600}$ was 0.5. The medium contained 2 mM L-isoleucine, 26 mg/l kanamycin, 3 mg/l chloramphenicol and β-alanine in a final concentration of 20 mM. After 5 hours cultivation IPTG (isopropylthio-β-D-galactoside) in a final concentration of 1 mM was added to the medium in each instance. After 49 and 74 hours a specimen was taken, the cells were centrifuged off and the supernatant sterilized by filtration. The concentration of pantothenate in the supernatant was determined as described in example 6. The results are shown in Table 4.

TABLE 4

Accumulation of D-pantothenate in various strains of C. glutamicum

| | D-pantothenate (mg/l) after an incubation time of | |
|---|---|---|
| Strain | 49 hours | 74 hours |
| ATCC13032ΔilvA/ pECM3ilvBNCD pEKEx2 | 80 | 100 |
| ATCC13032ΔilvA/ pECM3ilvBNCD pEKEx2panBC | 920 | 980 |

What is claimed is:

1. An isolated polynucleotide from Corynebacterium comprising a nucleotide sequence selected from the group consisting of:
   a) a nucleotide sequence encoding the panB gene product, which is ketopantoate hydroxymethyltransferase, whose amino acid sequence is set forth in SEQ ID NO: 3; and
   b) a nucleotide sequence encoding the panC gene product, which is pantothenate synthetase, whose amino acid sequence is set forth in SEQ ID NO: 4.

2. The isolated polynucleotide of claim 1, wherein the nucleotide sequence is selected from the group consisting of:
   a) the nucleotide sequence set forth in SEQ ID NO: 1, nucleotides 351–1163; and
   b) the nucleotide sequence set forth in SEQ ID NO: 1, nucleotides 1166–2002.

3. The isolated polynucleotide of claim 1, wherein the nucleotide sequence encodes the panB gene product, which is ketopantoate hydroxymethyltransferase, whose amino acid sequence is set forth in SEQ ID NO: 3, and wherein the nucleotide sequence also encodes the panC gene product, which is pantothenate synthetase, whose amino acid sequence is set forth in SEQ ID NO: 4.

4. The isolated polynucleotide of claim 3, wherein the nucleotide sequence contains the nucleotide sequence set forth in SEQ ID NO: 1, nucleotides 351–1163, and wherein the nucleotide sequence contains the nucleotide sequence set forth in SEQ ID NO: 1, nucleotides 1166–2002.

5. The isolated polynucleotide of claim 4, wherein the nucleotide sequence contains the panBC operon as set forth in SEQ ID NO: 1.

6. An isolated polynucleotide from Corynebacterium comprising a nucleotide sequence which hybridizes to the antisense strand of SEQ ID NO: 1 and that encodes an enzyme selected from the group consisting of ketopantoate hydroxymethyltransferase and pantothenate synthetase.

7. A vector comprising the isolated polynucleotide of claim 6.

8. The vector of claim 7 that is the shuttle vector pEKEx2panBC, characterized by the restriction map shown in FIG. 2 and deposited in *E. coli* strain DH5αmcr/pEKEx2panBC under the designation DSM 12456.

9. The vector of claim 7 that is the shuttle vector pECM3ilvBNCD, characterized by the restriction map shown in FIG. 3 and deposited in *E. coli* strain DH5αmcr/pECM3ilvBNCD under the designation DSM 12457.

10. A microorganism comprising the vector of claim 7.

11. The microorganism of claim 10, wherein said microorganism is from the genus Corynebacterium.

12. A method for producing pantothenic acid comprising:
a) transforming a vector into a microorganism to produce a recombinant microorganism, wherein said vector comprises a panB gene and a panC gene, both genes being operably linked to a suitable regulatory sequence;
b) growing said recombinant microorganism under conditions suitable for the production of pantothenic acid in an appropriate culture medium; and
c) recovering pantothenic acid from said culture medium;
wherein said panB gene encodes ketopantoate hydroxymethyltransferase, said panC gene encodes pantothenate synthetase, and both said panB and said panC genes originate from Corynebacterium.

13. The method of claim 12 comprising:
transforming, in addition to said vector comprising a panB gene and a panC gene,
a vector comprising a ilvD gene operably linked to a suitable regulatory sequence;
wherein said ilvD gene encodes dihydroxy acid dehydratase and originates from Corynebacterium.

14. The method of claim 12 comprising:
transforming, in addition to said vector comprising a panB gene and a panC gene,
a vector comprising a ilvBNCD operon operably linked to a suitable regulatory sequence;
wherein said ilvBNCD operon encodes acetohydroxy acid synthetase, acetohydroxy isomero reductase, and dihydroxy acid dehydratase and said ilvBNCD operon originates from Corynebacterium.

15. The method of any one of claims 12, 13, and 14, wherein the ilvA gene, encoding threonine dehydratase, is inactivated in said microorganism.

16. The method of any one of claims 12, 13, and 14, wherein said vector comprising a panB gene and a panC gene is the shuttle vector pEKEx2panBC and wherein said microorganism is from the genus Corynebacterium.

17. The method of claim 14, wherein said vector comprising a ilvBNCD operon is the shuttle vector pECM3ilvBNCD and wherein said microorganism is from the genus Corynebacterium.

18. The method of claim 14, wherein said vector comprising a panB gene and a panC gene is the shuttle vector pEKEx2panBC, and wherein said vector comprising a ilvBNCD operon is the shuttle vector pECM3ilvBNCD and wherein said microorganism is from the genus Corynebacterium.

19. The method of any one of claims 12, 13, and 14, wherein said microorganism is from the genus Corynebacterium.

20. The method of any one of claims 12, 13, and 14, wherein said transforming results in the introduction of multiple copies of said vectors into said microorganism.

21. A method for producing pantothenic acid in Corynebacterium comprising:
a) inserting an expression cassette upstream from the panB and panC genes in said Corynebacterium;
b) growing said Corynebacterium under conditions suitable for the production of pantothenic acid in an appropriate culture medium; and
c) recovering pantothenic acid from said culture medium.

22. A method for producing pantothenic acid in Corynebacterium comprising:
a) inserting expression cassettes upstream from the panB, panC and ilvD genes in said Corynebacterium;
b) growing said Corynebacterium under conditions suitable for the production of pantothenic acid in an appropriate culture medium; and
c) recovering pantothenic acid from said culture medium.

23. A method for producing pantothenic acid in Corynebacterium comprising:
a) increasing the stability of the mRNA which is translated from the panB and panC genes in said Corynebacterium; and/or
b) preventing the degradation of the panB and panC gene products in said Corynebacterium, which gene products are ketopantoate hydroxymethyltransferase and pantothenate synthetase, respectively;
wherein said Corynebacterium is grown under conditions suitable for the production of pantothenic acid in an appropriate culture medium, and wherein pantothenic acid is recovered from said culture medium.

24. The method of any one of claims 12, 13, and 14, wherein expression of the genes on the transformed vector or vectors is enhanced by altering the culture medium and/or the conduction of the growth.

25. The method of any one of claims 12, 13, 14, 21, 22, and 23, wherein the culture medium is altered by the addition of a precursor of pantothenic acid selected from the group consisting of aspartate, β-alanine, ketoisovalerate, ketopantoate, and pantoate.

* * * * *

SEQUENCE LISTING

<160> NUMBER OF SEQ ID NOS: 9

<210> SEQ ID NO 1
<211> LENGTH: 2164
<212> TYPE: DNA
<213> ORGANISM: Corynebacterium glutamicum

<400> SEQUENCE: 1

```
gcttcggggt accaattcct ttaagaacca tcagatcaat ctgttgtaca ttctcggcca      60
gattcagctt ttcggtaagg acgaaacact ttcacttgaa tcggcagcaa agtttcttaa     120
agtttctaag gcaactgcaa cgaggtattt tagaactctc cgagaaatgg aattagttca     180
cgaggtcagc aaacgccctt tgcggtttgc gctcacggat aaaggtcgtg agatagtagg     240
tcttgaggta aaaatttgac tccataacga gaacttaatc gagcaacacc cctgaacagt     300
gaatcaaatc ggaatttatt tattctgagc tggtcatcac atctatactc atgcccatgt     360
caggcattga tgcaaagaaa atccgcaccc gtcatttccg cgaagctaaa gtaaacggcc     420
agaaagtttc ggttctcacc agctatgatg cgctttcggc gcgcattttt gatgaggctg     480
gcgtcgatat gctccttgtt ggtgattccg ctgccaacgt tgtgctgggt cgcgatacca     540
ccttgtcgat caccttggat gagatgattg tgctggccaa ggcggtgacg atcgctacga     600
agcgtgcgct tgtggtggtt gatctgccgt ttggtaccta tgaggtgagc ccaaatcagg     660
cggtggagtc cgcgatccgg gtcatgcgtg aaacgggtgc ggctgcggtg aagatcgagg     720
gtggcgtgga gatcgcgcag acgattcgac gcattgttga tgctggaatt ccggttgtcg     780
gccacatcgg gtacacoccg cagtccgagc attccttggg cggccacgtg gttcagggtc     840
gtggcgcgag ttctggaaag ctcatcgccg atgcccgcgc gttggagcag gcgggtgcgt     900
ttgcggttgt gttggagatg gttccagcag aggcagcgcg cgaggttacc gaggatcttt     960
ccatcaccac tatcggaatc ggtgccggca atggcacaga tgggcaggtt ttggtgtggc    1020
```

-continued

```
aggatgcctt cggcctcaac cgcggcaaga agccacgctt cgtccgcgag tacgccacct    1080
tgggcgattc cttgcacgac gccgcgcagg cctacatcgc cgatatccac gcgggtacct    1140
tcccaggcga agcggagtcc tttaatgca ggtagcaacc acaaagcagg cgcttatcga    1200
cgccctcctc caccacaaat ccgtcgggct cgtccccacc atgggtgcgc tacacagcgg    1260
acacgcctcg ttggttaaag cagcacgcgc tgaaaacgac actgttgtag ccagtatttt    1320
tgtcaatccc ctgcagtttg aagcactcgg tgattgcgat gattaccgca actatccccg    1380
ccaactcgac gccgatttag cactgcttga gaggcaggt gtggatattg tgttcgcacc    1440
cgatgtggag gaaatgtacc ccggtggctt gccactagtg tgggcgcgca ccggttccat    1500
cggaacaaaa ttggagggtg ccagcaggcc tggccatttc gatggtgtgg ctaccgtggt    1560
ggcgaagctg ttcaatttgg tgcgccctga tcgtgcatat tttggacaaa agatgctca    1620 gcaggttgcg gtgattcggc gattggttgc cgatctagac attcccgtgg agattcgtcc    1680
cgttccgatt attcgtggcg ccgatggctt agccgaatcc agccgcaatc aacgtctttc    1740
tgcggatcag cgagcgcaag ctctggtgct gccgcaggtg ttgagtgggt tgcagcgtcg    1800
aaaagcagct ggtgaagcgc tagatatcca aggtgcgcgc gacaccttgg ccagcgccga    1860
cggcgtgcgc ttggatcacc tggaaattgt cgatccagcc accctcgaac cattagaaat    1920
cgacggcctg ctcacccaac cagcgttggt ggtcggcgcg attttcgtgg ggccggtgcg    1980
gttgatcgac aatatcgagc tctagtacca accctgcgtt gcagcacgca gcttcgcata    2040
acgcgtgctc agctcagtgt ttttaggtgc gcggtgcgga tcggaaccgg gagttggcca    2100
ctgcggtggc gtggcctcac ccgacagcgc ccatgccgcc tgacgagctg cacccaacgc    2160
caca                                                               2164
```

<210> SEQ ID NO 2
<211> LENGTH: 271
<212> TYPE: PRT
<213> ORGANISM: Corynebacterium glutamicum

<400> SEQUENCE: 2

```
Met Pro Met Ser Gly Ile Asp Ala Lys Lys Ile Arg Thr Arg His Phe
  1               5                  10                  15

Arg Glu Ala Lys Val Asn Gly Gln Lys Val Ser Val Leu Thr Ser Tyr
                 20                  25                  30

Asp Ala Leu Ser Ala Arg Ile Phe Asp Glu Ala Gly Val Asp Met Leu
             35                  40                  45

Leu Val Gly Asp Ser Ala Ala Asn Val Val Leu Gly Arg Asp Thr Thr
         50                  55                  60

Leu Ser Ile Thr Leu Asp Glu Met Ile Val Leu Ala Lys Ala Val Thr
 65                  70                  75                  80

Ile Ala Thr Lys Arg Ala Leu Val Val Asp Leu Pro Phe Gly Thr
                 85                  90                  95

Tyr Glu Val Ser Pro Asn Gln Ala Val Glu Ser Ala Ile Arg Val Met
                100                 105                 110

Arg Glu Thr Gly Ala Ala Val Lys Ile Glu Gly Gly Val Glu Ile
             115                 120                 125

Ala Gln Thr Ile Arg Arg Ile Val Asp Ala Gly Ile Pro Val Val Gly
         130                 135                 140

His Ile Gly Tyr Thr Pro Gln Ser Glu His Ser Leu Gly Gly His Val
145                 150                 155                 160
```

```
Val Gln Gly Arg Gly Ala Ser Ser Gly Lys Leu Ile Ala Asp Ala Arg
                165                 170                 175

Ala Leu Glu Gln Ala Gly Ala Phe Ala Val Val Leu Glu Met Val Pro
            180                 185                 190

Ala Glu Ala Ala Arg Glu Val Thr Glu Asp Leu Ser Ile Thr Thr Ile
        195                 200                 205

Gly Ile Gly Ala Gly Asn Gly Thr Asp Gly Gln Val Leu Val Trp Gln
    210                 215                 220

Asp Ala Phe Gly Leu Asn Arg Gly Lys Lys Pro Arg Phe Val Arg Glu
225                 230                 235                 240

Tyr Ala Thr Leu Gly Asp Ser Leu His Asp Ala Ala Gln Ala Tyr Ile
                245                 250                 255

Ala Asp Ile His Ala Gly Thr Phe Pro Gly Glu Ala Glu Ser Phe
            260                 265                 270

<210> SEQ ID NO 3
<211> LENGTH: 279
<212> TYPE: PRT
<213> ORGANISM: Corynebacterium glutamicum

<400> SEQUENCE: 3

Met Gln Val Ala Thr Thr Lys Gln Ala Leu Ile Asp Ala Leu Leu His
 1               5                  10                  15

His Lys Ser Val Gly Leu Val Pro Thr Met Gly Ala Leu His Ser Gly
                20                  25                  30

His Ala Ser Leu Val Lys Ala Ala Arg Ala Glu Asn Asp Thr Val Val
            35                  40                  45

Ala Ser Ile Phe Val Asn Pro Leu Gln Phe Glu Ala Leu Gly Asp Cys
    50                  55                  60

Asp Asp Tyr Arg Asn Tyr Pro Arg Gln Leu Asp Ala Asp Leu Ala Leu
65                  70                  75                  80

Leu Glu Glu Ala Gly Val Asp Ile Val Phe Ala Pro Asp Val Glu Glu
                85                  90                  95

Met Tyr Pro Gly Gly Leu Pro Leu Val Trp Ala Arg Thr Gly Ser Ile
            100                 105                 110

Gly Thr Lys Leu Glu Gly Ala Ser Arg Pro Gly His Phe Asp Gly Val
        115                 120                 125

Ala Thr Val Val Ala Lys Leu Phe Asn Leu Val Arg Pro Asp Arg Ala
    130                 135                 140

Tyr Phe Gly Gln Lys Asp Ala Gln Gln Val Ala Val Ile Arg Arg Leu
145                 150                 155                 160

Val Ala Asp Leu Asp Ile Pro Val Glu Ile Arg Pro Val Pro Ile Ile
                165                 170                 175

Arg Gly Ala Asp Gly Leu Ala Glu Ser Ser Arg Asn Gln Arg Leu Ser
            180                 185                 190

Ala Asp Gln Arg Ala Gln Ala Leu Val Leu Pro Gln Val Leu Ser Gly
        195                 200                 205

Leu Gln Arg Arg Lys Ala Ala Gly Glu Ala Leu Asp Ile Gln Gly Ala
    210                 215                 220

Arg Asp Thr Leu Ala Ser Ala Asp Gly Val Arg Leu Asp His Leu Glu
225                 230                 235                 240

Ile Val Asp Pro Ala Thr Leu Glu Pro Leu Glu Ile Asp Gly Leu Leu
                245                 250                 255

Thr Gln Pro Ala Leu Val Val Gly Ala Ile Phe Val Gly Pro Val Arg
            260                 265                 270
```

Leu Ile Asp Asn Ile Glu Leu
    275

<210> SEQ ID NO 4
<211> LENGTH: 2952
<212> TYPE: DNA
<213> ORGANISM: Corynebacterium glutamicum
<220> FEATURE:
<221> NAME/KEY: CDS
<222> LOCATION: (290)..(2125)

<400> SEQUENCE: 4

| | |
|---|---|
| agtacttgga gcgccaaaag gcactgggca agccagttca gttgaacttc gatgacgaca | 60 |
| ccgatgggaa tacaacacaa acagaaagcg ttgaatccca agagaccgga caagccgcgt | 120 |
| ctgaaacctc acatcgtgat aaccctgcgt cacagcacta gagtgtaata agccgtccga | 180 |
| accaaaggtc cacacctctg cacgagtaga agctcaccca agttttcaaa gtgccgttga | 240 |
| ttcttgacaa ccacccgccg ctctttagag cagatttgaa aagcgcatc atg atc cca | 298 |
|                                                              Met Ile Pro |
|                                                                  1 |

| | |
|---|---|
| ctt cgt tca aaa gtc acc acc gtc ggt cgc aat gca gct ggc gct cgc | 346 |
| Leu Arg Ser Lys Val Thr Thr Val Gly Arg Asn Ala Ala Gly Ala Arg | |
|       5              10                  15                     | |
| gcc ctt tgg cgt gcc acc ggc acc aag gaa aat gag ttc ggc aag cca | 394 |
| Ala Leu Trp Arg Ala Thr Gly Thr Lys Glu Asn Glu Phe Gly Lys Pro | |
|  20              25                  30                  35     | |
| att gtt gcc atc gta aac tcc tac acc cag ttc gtg ccc gga cac gtt | 442 |
| Ile Val Ala Ile Val Asn Ser Tyr Thr Gln Phe Val Pro Gly His Val | |
|              40                  45                  50         | |
| cac ctt aag aac gtc ggc gat att gtg gca gat gca gtg cgc aaa gcc | 490 |
| His Leu Lys Asn Val Gly Asp Ile Val Ala Asp Ala Val Arg Lys Ala | |
|          55                  60                  65             | |
| ggt ggc gtt cca aag gaa ttc aac acc atc gtc gat gac ggc atc gcc | 538 |
| Gly Gly Val Pro Lys Glu Phe Asn Thr Ile Val Asp Asp Gly Ile Ala | |
|      70                  75                  80                 | |
| atg gga cac ggc ggc atg ctg tac tcc ctg cca tcc cgt gaa atc atc | 586 |
| Met Gly His Gly Gly Met Leu Tyr Ser Leu Pro Ser Arg Glu Ile Ile | |
|  85                  90                  95                     | |
| gcc gac tcc gtc gaa tac atg gtc aac gca cac acc gcc gac gcc atg | 634 |
| Ala Asp Ser Val Glu Tyr Met Val Asn Ala His Thr Ala Asp Ala Met | |
| 100             105                 110                 115     | |
| gtg tgt atc tcc aac tgt gac aag atc acc cca ggc atg ctc aac gca | 682 |
| Val Cys Ile Ser Asn Cys Asp Lys Ile Thr Pro Gly Met Leu Asn Ala | |
|             120                 125                 130         | |
| gca atg cgc ctg aac atc cca gtg gtc ttc gtt tcc ggt ggc cca atg | 730 |
| Ala Met Arg Leu Asn Ile Pro Val Val Phe Val Ser Gly Gly Pro Met | |
|         135                 140                 145             | |
| gaa gct ggc aag gct gtc gtc gtt gag cgc gtt gca cac gca cca acc | 778 |
| Glu Ala Gly Lys Ala Val Val Val Glu Arg Val Ala His Ala Pro Thr | |
|     150                 155                 160                 | |
| gac ctc atc acc gcg atc tcc gca tcc gca agc gat gca gtc gac gac | 826 |
| Asp Leu Ile Thr Ala Ile Ser Ala Ser Ala Ser Asp Ala Val Asp Asp | |
| 165                 170                 175                     | |
| gca ggc ctt gca gcc gtt gaa cga tcc gca tgc cca acc tgt ggc tcc | 874 |
| Ala Gly Leu Ala Ala Val Glu Arg Ser Ala Cys Pro Thr Cys Gly Ser | |
| 180                 185                 190                 195 | |
| tgc tcc ggt atg ttc acc gcg aac tcc atg aac tgc ctc acc gaa gct | 922 |
| Cys Ser Gly Met Phe Thr Ala Asn Ser Met Asn Cys Leu Thr Glu Ala | |
|             200                 205                 210         | |

| | | |
|---|---|---|
| ctg gga ctt tct ctc ccg ggc aac ggc tcc act ctg gca acc cac gca<br>Leu Gly Leu Ser Leu Pro Gly Asn Gly Ser Thr Leu Ala Thr His Ala<br>215 220 225 | | 970 |
| gca cgt cgc gca ctg ttt gaa aag gcc ggc gaa acc gtc gtt gaa ctg<br>Ala Arg Arg Ala Leu Phe Glu Lys Ala Gly Glu Thr Val Val Glu Leu<br>230 235 240 | | 1018 |
| tgc cgc cgc tac tac ggt gaa gaa gac gaa tcc gtt ctg cca cgt ggc<br>Cys Arg Arg Tyr Tyr Gly Glu Glu Asp Glu Ser Val Leu Pro Arg Gly<br>245 250 255 | | 1066 |
| att gcc acc aag aag gca ttc gaa aac gca atg gca ctg gat atg gcc<br>Ile Ala Thr Lys Lys Ala Phe Glu Asn Ala Met Ala Leu Asp Met Ala<br>260 265 270 275 | | 1114 |
| atg ggt gga tcc acc aac acc atc ctc cac atc ctc gca gct gcc cag<br>Met Gly Gly Ser Thr Asn Thr Ile Leu His Ile Leu Ala Ala Ala Gln<br>280 285 290 | | 1162 |
| gaa ggc gaa gtt gac ttc gac ctc gca gac atc gac gaa ctg tcc aaa<br>Glu Gly Glu Val Asp Phe Asp Leu Ala Asp Ile Asp Glu Leu Ser Lys<br>295 300 305 | | 1210 |
| aac gtc ccc tgc ctg tcc aag gtt gca cca aac tcc gac tac cac atg<br>Asn Val Pro Cys Leu Ser Lys Val Ala Pro Asn Ser Asp Tyr His Met<br>310 315 320 | | 1258 |
| gaa gac gtc cac cgc gcc ggt cgc att cca gca ctg ctc ggc gag ctc<br>Glu Asp Val His Arg Ala Gly Arg Ile Pro Ala Leu Leu Gly Glu Leu<br>325 330 335 | | 1306 |
| aac cgc ggt ggc ctg ctg aac aag gac gtc cac tcc gtt cac tcc aac<br>Asn Arg Gly Gly Leu Leu Asn Lys Asp Val His Ser Val His Ser Asn<br>340 345 350 355 | | 1354 |
| gac ctt gaa ggt tgg ttg gat gac tgg gat atc cgc tct ggc aag acc<br>Asp Leu Glu Gly Trp Leu Asp Asp Trp Asp Ile Arg Ser Gly Lys Thr<br>360 365 370 | | 1402 |
| acc gaa gta gca acc gaa ctc ttc cac gca gcc cca ggt ggc atc cgc<br>Thr Glu Val Ala Thr Glu Leu Phe His Ala Ala Pro Gly Gly Ile Arg<br>375 380 385 | | 1450 |
| acc acc gaa gca ttc tcc acc gag aac cgc tgg gac gaa ctc gac acc<br>Thr Thr Glu Ala Phe Ser Thr Glu Asn Arg Trp Asp Glu Leu Asp Thr<br>390 395 400 | | 1498 |
| gac gct gcc aag ggc tgc atc cgc gac gtt gaa cac gcc tac acc gcc<br>Asp Ala Ala Lys Gly Cys Ile Arg Asp Val Glu His Ala Tyr Thr Ala<br>405 410 415 | | 1546 |
| gac ggc ggc ctg gtt gtt ctt cgc ggc aac atc tcc cct gac ggc gca<br>Asp Gly Gly Leu Val Val Leu Arg Gly Asn Ile Ser Pro Asp Gly Ala<br>420 425 430 435 | | 1594 |
| gtg atc aag tcc gca ggt atc gaa gaa gag ctg tgg aac ttc acc gga<br>Val Ile Lys Ser Ala Gly Ile Glu Glu Glu Leu Trp Asn Phe Thr Gly<br>440 445 450 | | 1642 |
| cca gca cga gtt gtc gaa agc cag gaa gag gca gtc tct gtc atc ctg<br>Pro Ala Arg Val Val Glu Ser Gln Glu Glu Ala Val Ser Val Ile Leu<br>455 460 465 | | 1690 |
| acc aag acc atc caa gct ggc gaa gtt ctg gtc gtc cgc tac gaa ggc<br>Thr Lys Thr Ile Gln Ala Gly Glu Val Leu Val Val Arg Tyr Glu Gly<br>470 475 480 | | 1738 |
| cca tca ggt gga cca ggc atg cag gaa atg ctt cac cca acc gca ttc<br>Pro Ser Gly Gly Pro Gly Met Gln Glu Met Leu His Pro Thr Ala Phe<br>485 490 495 | | 1786 |
| ctc aag gga tcc ggc ctg ggc aag aag tgt gca ctg atc acc gac ggc<br>Leu Lys Gly Ser Gly Leu Gly Lys Lys Cys Ala Leu Ile Thr Asp Gly<br>500 505 510 515 | | 1834 |
| cgt ttc tcc gga ggt tcc tca gga ctg tcc atc ggc cac gtc tcc cca<br>Arg Phe Ser Gly Gly Ser Ser Gly Leu Ser Ile Gly His Val Ser Pro<br>520 525 530 | | 1882 |

```
gaa gca gca cac ggc gga gtc att ggt ctg atc gaa aac ggc gac atc          1930
Glu Ala Ala His Gly Gly Val Ile Gly Leu Ile Glu Asn Gly Asp Ile
                535                 540                 545 gtc tcc atc gac gtt cac aac cgc aag ctc gaa gtt cag gtc tcc gac          1978
Val Ser Ile Asp Val His Asn Arg Lys Leu Glu Val Gln Val Ser Asp
            550                 555                 560 gag gaa ctc cag cgc cgc cgc gac gct atg aac gcc tcc gag aag cca          2026
Glu Glu Leu Gln Arg Arg Arg Asp Ala Met Asn Ala Ser Glu Lys Pro
        565                 570                 575 tgg cag cca gtc aac cgt aac cgc gtt gtc acc aag gca ctg cgc gca          2074
Trp Gln Pro Val Asn Arg Asn Arg Val Val Thr Lys Ala Leu Arg Ala
580                 585                 590                 595 tac gca aag atg gct acc tcc gct gat aag ggt gca gtc cgt cag gtc          2122
Tyr Ala Lys Met Ala Thr Ser Ala Asp Lys Gly Ala Val Arg Gln Val
                600                 605                 610 gac taaccctttg tgagtgtttg agcaccggtt ccctactttg ggttccggtg               2175
Asp cttttcatg tcttggcctg tgtgggcgtg gtggagctcc ccgttgcaaa tactcaccac         2235
aagttgcagg atttctgctg gttgtggtgg attttcccgc tttatagccc tatgcgtgca        2295
actttcggac cgattccaaa gggcaaagcc ctgtttgtgg tggatccttg ccctggaagc        2355
tttcaggaac cacaactacc ccactgaccc caaagtggat aggccctatt cttccgttta        2415
agcgcctcaa acacctctcc ccacacttga cccattaggc aattacgaat ccttaaacag        2475
ccttctacag caccatgccc caaaccgaac ccaggcatga aaaagaccct caccaggagg        2535
gtctttttct aaaactttgg ctacgcgatt gggttcacac ccgcaccgaa ccaccacagc        2595
agaactgccg ctgcgatgcc gatgaccacg aagatccacg agctcaccag tggacgcttt       2655
gcccaacctc ggccagagtc aagggaaatc ttgccggggc cggtgaactg aagtccgaca        2715
accacgatag tgaggatcag tgccagcatc aatggctcac taagttcacc ccaaccacct       2775
tcatgagtgt tgacttggtg aagggtggta aaggatgtcg ccaccgtggc taccgctgct       2835
gccactgggg tcatcagacc aaggagcagg aagacaccag ccgcaagttc aatagatgga       2895
agcaggatcg cgaggatttc aggccactgg taaccagcga actctgcctc gactcta         2952
```

```
<210> SEQ ID NO 5
<211> LENGTH: 612
<212> TYPE: PRT
<213> ORGANISM: Corynebacterium glutamicum

<400> SEQUENCE: 5

Met Ile Pro Leu Arg Ser Lys Val Thr Thr Val Gly Arg Asn Ala Ala
  1               5                  10                  15

Gly Ala Arg Ala Leu Trp Arg Ala Thr Gly Thr Lys Glu Asn Glu Phe
                 20                  25                  30

Gly Lys Pro Ile Val Ala Ile Val Asn Ser Tyr Thr Gln Phe Val Pro
             35                  40                  45

Gly His Val His Leu Lys Asn Val Gly Asp Ile Val Ala Asp Ala Val
         50                  55                  60

Arg Lys Ala Gly Gly Val Pro Lys Glu Phe Asn Thr Ile Val Asp Asp
 65                  70                  75                  80

Gly Ile Ala Met Gly His Gly Gly Met Leu Tyr Ser Leu Pro Ser Arg
                 85                  90                  95

Glu Ile Ile Ala Asp Ser Val Glu Tyr Met Val Asn Ala His Thr Ala
            100                 105                 110
```

-continued

```
Asp Ala Met Val Cys Ile Ser Asn Cys Asp Lys Ile Thr Pro Gly Met
        115                 120                 125

Leu Asn Ala Ala Met Arg Leu Asn Ile Pro Val Val Phe Val Ser Gly
        130                 135                 140

Gly Pro Met Glu Ala Gly Lys Ala Val Val Glu Arg Val Ala His
145                 150                 155                 160

Ala Pro Thr Asp Leu Ile Thr Ala Ile Ser Ala Ser Ala Ser Asp Ala
                165                 170                 175

Val Asp Asp Ala Gly Leu Ala Ala Val Glu Arg Ser Ala Cys Pro Thr
                180                 185                 190

Cys Gly Ser Cys Ser Gly Met Phe Thr Ala Asn Ser Met Asn Cys Leu
                195                 200                 205

Thr Glu Ala Leu Gly Leu Ser Leu Pro Gly Asn Gly Ser Thr Leu Ala
        210                 215                 220

Thr His Ala Ala Arg Arg Ala Leu Phe Glu Lys Ala Gly Glu Thr Val
225                 230                 235                 240

Val Glu Leu Cys Arg Arg Tyr Tyr Gly Glu Glu Asp Glu Ser Val Leu
                245                 250                 255

Pro Arg Gly Ile Ala Thr Lys Lys Ala Phe Glu Asn Ala Met Ala Leu
                260                 265                 270

Asp Met Ala Met Gly Gly Ser Thr Asn Thr Ile Leu His Ile Leu Ala
        275                 280                 285

Ala Ala Gln Glu Gly Glu Val Asp Phe Asp Leu Ala Asp Ile Asp Glu
        290                 295                 300

Leu Ser Lys Asn Val Pro Cys Leu Ser Lys Val Ala Pro Asn Ser Asp
305                 310                 315                 320

Tyr His Met Glu Asp Val His Arg Ala Gly Arg Ile Pro Ala Leu Leu
                325                 330                 335

Gly Glu Leu Asn Arg Gly Gly Leu Leu Asn Lys Asp Val His Ser Val
                340                 345                 350

His Ser Asn Asp Leu Glu Gly Trp Leu Asp Asp Trp Asp Ile Arg Ser
        355                 360                 365

Gly Lys Thr Thr Glu Val Ala Thr Glu Leu Phe His Ala Ala Pro Gly
        370                 375                 380

Gly Ile Arg Thr Thr Glu Ala Phe Ser Thr Glu Asn Arg Trp Asp Glu
385                 390                 395                 400

Leu Asp Thr Asp Ala Ala Lys Gly Cys Ile Arg Asp Val Glu His Ala
                405                 410                 415

Tyr Thr Ala Asp Gly Gly Leu Val Val Leu Arg Gly Asn Ile Ser Pro
                420                 425                 430

Asp Gly Ala Val Ile Lys Ser Ala Gly Ile Glu Glu Leu Trp Asn
        435                 440                 445

Phe Thr Gly Pro Ala Arg Val Val Glu Ser Gln Glu Glu Ala Val Ser
        450                 455                 460

Val Ile Leu Thr Lys Thr Ile Gln Ala Gly Glu Val Leu Val Val Arg
465                 470                 475                 480

Tyr Glu Gly Pro Ser Gly Gly Pro Gly Met Gln Glu Met Leu His Pro
                485                 490                 495

Thr Ala Phe Leu Lys Gly Ser Gly Leu Gly Lys Lys Cys Ala Leu Ile
                500                 505                 510

Thr Asp Gly Arg Phe Ser Gly Gly Ser Ser Gly Leu Ser Ile Gly His
                515                 520                 525

Val Ser Pro Glu Ala Ala His Gly Gly Val Ile Gly Leu Ile Glu Asn
```

-continued

```
                530                 535                 540
Gly Asp Ile Val Ser Ile Asp Val His Asn Arg Lys Leu Glu Val Gln
545                 550                 555                 560

Val Ser Asp Glu Glu Leu Gln Arg Arg Arg Asp Ala Met Asn Ala Ser
                565                 570                 575

Glu Lys Pro Trp Gln Pro Val Asn Arg Asn Arg Val Val Thr Lys Ala
                580                 585                 590

Leu Arg Ala Tyr Ala Lys Met Ala Thr Ser Ala Asp Lys Gly Ala Val
            595                 600                 605

Arg Gln Val Asp
    610
```

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence:Primer

<400> SEQUENCE: 6
gatcgtcgac catcacatct atactcatgc cc                                    32

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:Primer

<400> SEQUENCE: 7
acccgatgtg gccgacaacc                                                  20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 8
gttcgcaccc gatgtggagg                                                  20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:Primer

<400> SEQUENCE: 9
atgcacgatc agggcgcacc                                                  20